US00PP12136P2

(12) United States Plant Patent
Rother

(10) Patent No.: US PP12,136 P2
(45) Date of Patent: Oct. 9, 2001

(54) PETUNIA PLANT NAMED 'CHERRY CASCADE'

(76) Inventor: Reinhard W. Rother, P.B. 327, Emerald, Victoria (AU)

( * ) Notice: Subject to any disclaimer, the term of this patent is extended or adjusted under 35 U.S.C. 154(b) by 0 days.

(21) Appl. No.: 09/545,909

(22) Filed: Apr. 9, 2000

(51) Int. Cl.[7] ..... A01H 5/00
(52) U.S. Cl. ..... Plt./356

(58) Field of Search ..... Plt./356

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Petunia plant named 'Cherry Cascade', characterized by its initially upright then low spreading and cascading plant habit; freely and continuous branching; rapid growth rate, dark green leaves; relatively early flowering; and numerous dark reddish purple-colored flowers.

1 Drawing Sheet

BACKGROUND OF THE INVENTION

The present Invention relates to a new and distinct cultivar of Petunia plant, botanically known as *Petunia×hybrida*, and hereinafter referred to by the cultivar name Cherry Cascade.

The new Petunia is a product of a planned breeding program conducted by the Inventor in Emerald, Victoria, Australia. The new Petunia originated from a cross made by the Inventor of a proprietary selection of *Petunia×hybrida* identified as code number 121010 as the female, or seed, parent with a proprietary selection of *Petunia×hybrida* identified as a code number 121036 as the male, or pollen, parent. The new Petunia was selected in October, 1993 on the basis of its attractive flower color.

Plants of the new Petunia are more spreading and have smaller flowers than plants of the female parent selection. Compared to plants of the male parent selection, plants of the new Petunia are more compact, more spreading, and have smaller leaves and flowers.

Asexual reproduction of the new cultivar by terminal cuttings taken at Emerald, Victoria, Australia, has shown that the unique features of this new Petunia are stable and reproduced true to type in successive generations.

SUMMARY OF THE INVENTION

Plants of the cultivar Cherry Cascade have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Cherry Cascade'. These characteristics in combination distinguish 'Cherry Cascade' as a new and distinct cultivar:

1. Initially upright then low spreading and cascading plant habit.
2. Freely and continuous branching.
3. High vigor.
4. Dark green leaves.
5. Relatively early flowering.
6. Numerous dark reddish purple-colored flowers.

Plants of the cultivar Cherry Cascade can be compared to plants of the cultivar Pampas Fire, disclosed in U.S. Plant Pat. No. 9,408. However in side-by-side comparisons conducted by the Inventor in Emerald, Victoria, Australia, plants of the cultivar Cherry Cascade are more compact and have smaller flowers than plants of the cultivar Pampas Fire. In addition, plants of the new Petunia and Pampas Fire differ in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Petunia.

The photograph at the top of the sheet comprises a side perspective view of typical flowering plants of 'Cherry Cascade'.

The photograph at the bottom of the sheet is a close-up view of typical opened flowers showing the progression of color changes with development and the upper surface of a typical leaf of 'Cherry Cascade'.

DETAILED BOTANICAL DESCRIPTION

In the following description, color references are made to The Royal Horticultural Society Colour Chart except where general terms of ordinary dictionary significance are used. Plants grown in 25-cm containers were used for the following description with three plants per container. Plants were grown under full sun field conditions which closely approximate commercial production conditions during the spring in Bonsall, Calif. Day temperatures ranged from 13 to 35° C. and night temperatures ranged from 7 to 18° C.

Botanical classification: *Petunia×hybrida* cultivar Cherry Cascade.

Parentage:

*Female parent.*—Proprietary selection of *Petunia×hybrida* identified as code number 121010, not patented.

*Male parent.*—Proprietary selection of *Petunia*× *hybrida* identified as code number 121036, not patented.

Propagation:

*Type cutting.*—Terminal vegetative cuttings.

*Time to initiate roots, summer.*—About 10 to 12 days at 22° C.

*Time to initiate roots, winter.*—About 10 to 15 days at 22° C.

*Rooting habit.*—Numerous, fine, fibrous, and well-branched.

Plant description:

*Form.*—Indeterminate; initially upright, then low spreading and cascading; viscid and glandular pubescent.

*Usage.*—Apropriate for hanging baskets and patio containers.

*Crop time.*—About 8 weeks are required to produce finished flowering plants in 10-cm containers.

*Plant height* (*from soil level to top of plant plane*).—About 9 cm.

*Area of spread.*—About 29 cm.

*Vigor.*—Vigorous; rapid growth rate.

*Branching habit.*—Freely branching with about six to eight lateral branches per plant; removal of terminal apices (pinching) enhanches branching.

*Lateral branches.*—Length: About 38 cm. Diameter: About 2 mm. Internode length: About 2.75 cm. Texture: Pubescent; viscid, glandular. Color: 145B.

*Foliage description.*—Leaves simple, generally symmetrical and long persisting. Leaf arrangement opposite before flowering, opposite after flowering. Quantity per lateral branch: Typically about 30. Length: About 6 cm. Width: About 3.5 cm. Aspect: Typically horizontal. Shape: Obovate to elliptic. Apex: Broadly acute to rounded. Base: Attenuate. Margin: Entire. Texture: Slightly coarse; very sparse pubescence on both surfaces; glandular, viscid. Color: Young foliage, upper surface: 146B. Young foliage, lower surface: 146C. Mature foliage, upper surface: 137A; venation, 146C. Mature foliage, lower surface: 146C; venation, 146B to 146C. Petiole: Length: About 1.1 cm. Diameter: About 4 mm. Color: 146C.

Flower description:

*Flower type and habit.*—Small to medium-sized flowers; flowers face mostly upward or outward; single, axillary. Flowers persistent. Flowering continuous.

*Natural flowering season.*—Long day responsive; flowering from spring through fall. Plants starting flowering about four to six weeks after rooting.

*Quantity.*—Freely flowering with about 30 flowers and flower buds per plant.

*Fragrance.*—Slight spicy sweet fragrance.

*Flower longevity on the plant.*—About 5 to 6 days.

*Flower buds* (*just showing color*).—Length: About 2.25 cm. Diameter: About 5 mm. Shape: Elongate with slightly ruffled apices. Color: More gray than 83B.

*Corolla.*—Arrangement/appearance: Single whorl of five petals, fused into flared trumpet. Flower diameter: About 4 cm. Flower tube length: About 2.8 cm. Flower throat diameter, distal end: About 1 cm. Flower tube diameter, proximal end: About 2 mm. Petal length from throat: About 1.9 cm. Petal width: About 2 cm. Petal shape: Spatulate to fan-shaped. Petal apex: Obcordate. Petal margin: Entire; slightly sinuate. Texture: Smooth, satiny. Color: Petal, upper surface, when opening: Brighter and more saturated than 77A. Petal, lower surface, when opening: 77A to 77B. Petal, upper surface, opened flower: Slightly more blue than 74A; with development, bi-color effect with 78A central star surrounded by brighter than 77A; subsequently fading to 78A to 78B; veins, 78A. Petal, lower surface, opened flower: 78C; veins, 78C. Flower throat (inside): 79B to 79A; veins, 79A. Flower tube (outside): 79C to 79D; veins, 78C.

*Sepals.*—Quantity: Five. Shape: Strap-like; narrow; slightly spatulate. Apex: Rounded. Margin: Entire. Texture: Smooth with tiny white hairs. Color: Upper surface: 144A. Lower surface: 144B.

*Peduncle.*—Strength: Moderately strong. Angle: About 45° to 90° to the stem dependent on stem orientation. Length: About 1.6 cm. Color: 145A.

*Reproductive organs.*—Stamens: Stamen number per flower/arrangement: About five; adnate to corolla tube base. Anther shape: Ovoid. Anther length: About 2 mm. Anther color: 76A. Pollen amount: Scarce. Pollen color: 76B. Pistils: Pistil quantity per flower: One. Pistil length: About 1.8 cm. Stigma shape: Flattened; slightly bi-lobate. Stigma color: More gray than 91A. Style length: About 1.5 cm. Style color: 144D. Ovary color: 144C.

*Seed.*—Seed production has not been observed.

Disease resistance: Plants of the new Petunia have not been noted to be resistant to pathogens common to Petunia.

It is claimed:

1. A new and distinct cultivar of Petunia plant named 'Cherry Cascade', as illustrated and described.

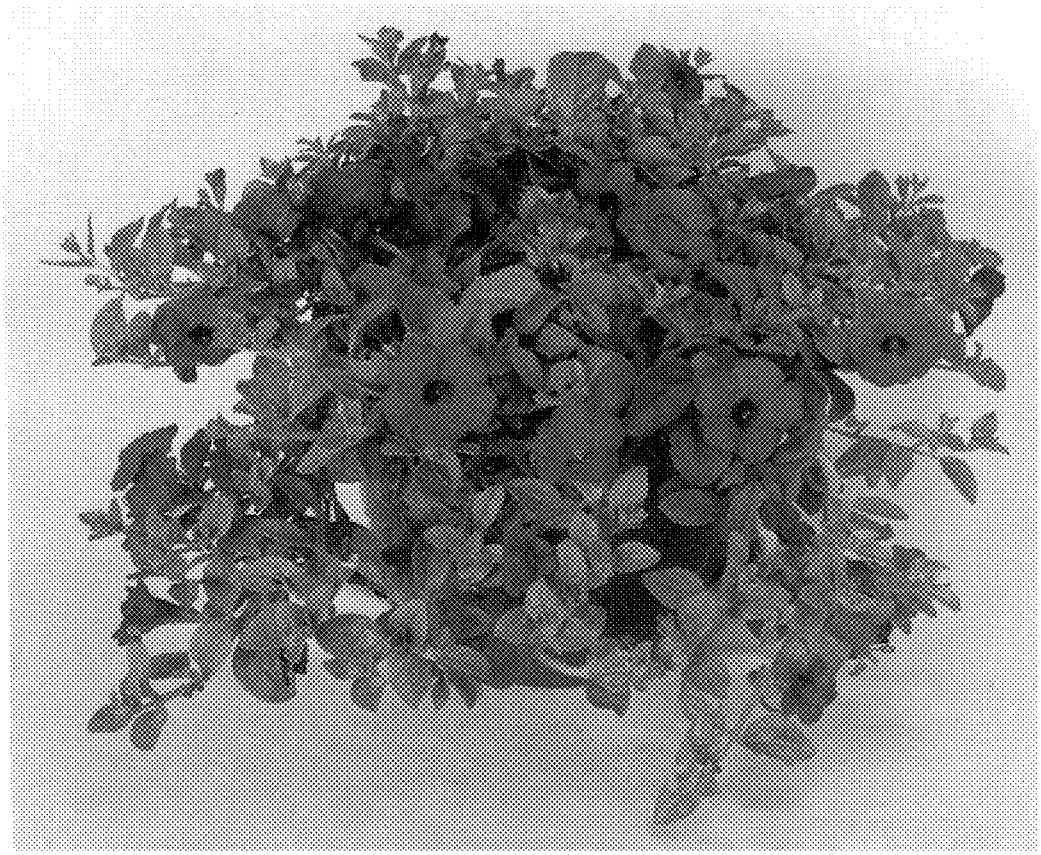
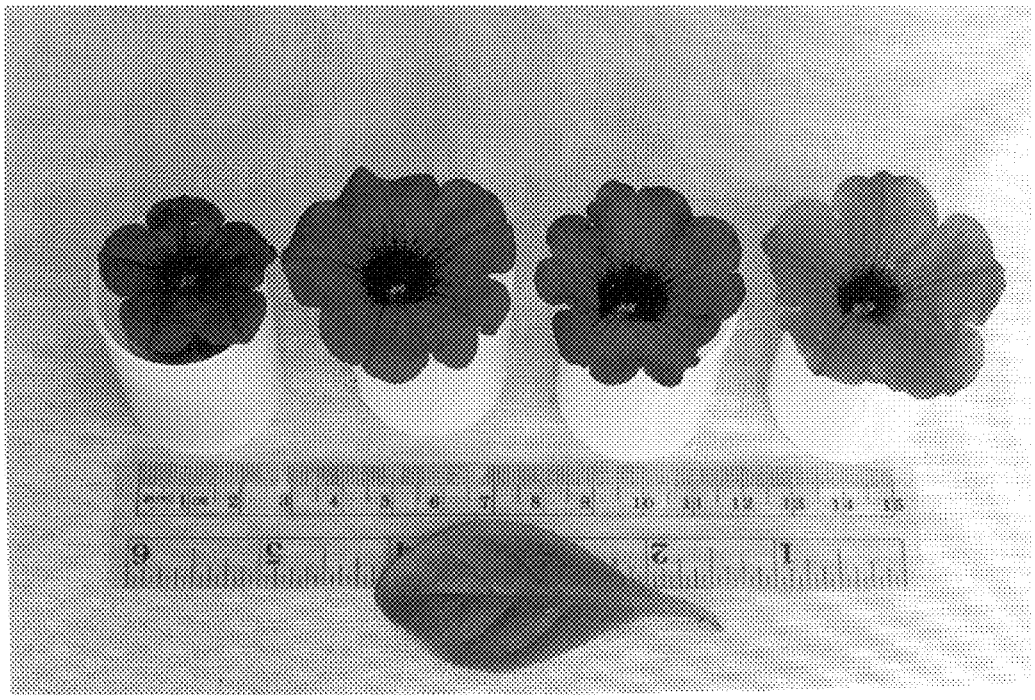

* * * * *